United States Patent
Molnar et al.

(10) Patent No.: US 6,246,785 B1
(45) Date of Patent: Jun. 12, 2001

(54) AUTOMATED, MICROSCOPE-ASSISTED EXAMINATION PROCESS OF TISSUE OR BODILY FLUID SAMPLES

(75) Inventors: Bela Molnar, Budapest (HU); Rainer Schäfer, München; Winfried Albert, Eberfing, both of (DE)

(73) Assignee: Roche Diagnostics GmbH (DE)

( * ) Notice: Subject to any disclaimer, the term of this patent is extended or adjusted under 35 U.S.C. 154(b) by 0 days.

(21) Appl. No.: 09/147,161

(22) PCT Filed: Apr. 25, 1997

(86) PCT No.: PCT/EP97/02130

§ 371 Date: Feb. 19, 1999

§ 102(e) Date: Feb. 19, 1999

(87) PCT Pub. No.: WO97/41416

PCT Pub. Date: Nov. 6, 1997

(30) Foreign Application Priority Data

Apr. 27, 1996 (DE) .............................................. 196 16 997

(51) Int. Cl.[7] ........................................................ G06K 9/00

(52) U.S. Cl. ............................................................ 382/133

(58) Field of Search .................................... 382/128, 133, 382/155, 156, 157, 158, 173, 224, 225, 226, 227, 266, 270, 275, 276; 356/36, 39, 364, 121, 122, 904, 388, 237.1, 436; 348/79, 80, 195, 202, 345, 349, 370

(56) References Cited

U.S. PATENT DOCUMENTS 4,965,725 * 10/1990 Rutenberg ............................ 382/224

(List continued on next page.)

FOREIGN PATENT DOCUMENTS

WO 91/20048   12/1991   (WO) .............................. G06F/15/42

OTHER PUBLICATIONS

"An integrated neural network systemfor histological image understanding", By Refenes et al., proceeding of SPIE, The international society for optical engineering, Bd. 1386, 1990, pp. 62–74.*

(List continued on next page.)

*Primary Examiner*—Andrew W. Johns
*Assistant Examiner*—Shervin Nakhjavan
(74) *Attorney, Agent, or Firm*—Marilyn L. Amick; Roche Diagnostics Corporation (57) ABSTRACT

Method for the automated, microscope-aided examination of tissue samples or samples of body fluids with the aid of neural networks. In a first method of examination the sample is firstly classified according to its type and subsequently a digitalized image is divided into connected segments which are examined by one or several neural networks. The sample is classified as pathological if cell types are present which do not belong to the type of sample or if structural cell or tissue changes are present.

In a second method of examination the digitalized image is again segmented and the segments are examined for the presence of a cell object. This is followed by an examination whether the cell object is an individual cell or a cell complex. In a third step of the analysis it is determined whether the found cell object is located on one of the image borders. If this is the case then a further image is recorded in which the found cell objects are completely included. Finally the segments in which cell objects have been detected are analysed at a higher magnification.

37 Claims, 5 Drawing Sheets

U.S. PATENT DOCUMENTS

| | | | |
|---|---|---|---|
| 5,313,532 | * | 5/1994 | Harvey et al. ............... 382/156 |
| 5,741,213 | * | 4/1998 | Kouchi et al. ............... 600/310 |
| 5,830,141 | * | 11/1998 | Makram-Ebeid et al. ....... 600/407 |
| 5,857,030 | * | 1/1999 | Gaborski et al. ............ 382/132 |

OTHER PUBLICATIONS

"Integration of neural networks and decision tree classifiers for automated cytology screening", By Shih–Jong Lee et al., IEEE International joint conference on neural networks, 1991, pp. I 257–I 261.*

"An automatic system for the classification of cellular categories in cytological images", By Revenu et al., Proceedings of SPIE, 1993, pp. 32–43.*

A.N. Refenes et al., "An Integrated Neural Network System for Histological Image Understanding" SPIE vol. 1386 Machine Vision Systems Integration in Industry (1990) pp. 62–74.

Marinette Revenu et al. "An Automatic System for the Classification of Cellular Categories in Cytological Images" SPIE vol. 2055 Intelligent Robots and Computer Vision XII (1993) pp. 32–43.

* cited by examiner

INPUT  HIDDEN  OUPUT

INPUTS  INPUT NEURON  NODE OUTPUT

Fig. 4 recording an image and digitalizing it

↓ segmenting the image

↓ classifying the type of sample

↓

| $NN_{\beta 1}$: is a cell/cell complex/ tissue parts or artefact structure present? | $NN_{\beta 2}$ is epithelium/ endothelium/ connective tissue/ musculature or body fluid present? | $NN_{\beta 3}$: is a cell or a cell complex present? | $NN_{\beta 4}$: does the cell object protrude over the edge of the segment? |

↓

| $NN_{\delta 1}$: are cell types present which do not belong to the type of sample? | $NN_{\delta 2}$: are structural cell/tissue changes present? |

↓ classification of the type of sample

Fig. 5

AUTOMATED, MICROSCOPE-ASSISTED EXAMINATION PROCESS OF TISSUE OR BODILY FLUID SAMPLES

The present invention concerns a method for examining tissue samples or body fluids on a slide with an automatic microscope as well as a video system and an evaluation computer with neural networks. The details of the method follow from the claims 1 and 8.

In the state of the art computer-aided image analysis systems are known for examining samples which comprise a microscope with a video camera coupled to a computer. The image recorded by the video camera is transferred with the aid of an image processing chip to the computer and displayed in a suitable manner on a screen using an imaging processing software. In the known procedure of the state of the art the user has to adjust and focus the microscope on the area to be examined. The sample is analysed on the basis of the image shown on the screen which can be optionally aided by the image processing software by changes in the contrast, colouration etc.

Instrumentation with a greater degree of automation is also known in the state of the art as for example described in WO 91/20048 and WO 92/13308. The devices disclosed in these documents have an automatic microscope with a camera and a computer-aided analysis system. Lens changes, focussing and sample movement are carried out automatically. The analysis is carried out by abstracting the background from the image information by special methods such as e.g. threshold methods.

Objects are located within the image and separated from one another. The located objects (usually cells) are focussed and morphometric and densitometric parameters are determined. These parameters are subsequently evaluated by rule-based or multivariate statistical methods. A requirement for this procedure is that cells in close proximity can be optically separated from one another since otherwise cells cannot be recognized on the basis of morphometric and densitometric parameters. Such a procedure is described in the article "Automated Cervical Smear Classification" (IEEE/9th Annual Conference of the Engineering in Medicine and Biological Society, page 1457). In this article it is proposed that the problem of overlapping cells can be solved by only staining the nuclei and carrying out the classification on the basis of this staining.

Furthermore mathematical optimization methods are known in the state of the art which attempt to separate the images of the objects from one another in a multivariable space by separation lines/separation areas. Rule-based and statistical methods have also been developed to solve the problem of object separation.

The object of the present invention was to provide a method for examining tissue samples or body fluid samples which enables a specific analysis even for samples with objects in close proximity without having to focus and separate objects.

The aforementioned object is achieved by a method as claimed in claim 1 and claim 8. In particular it has turned out to be important for examining the sample with a neural network that an image of the cells, cell complexes or histological structures is formed in such a way that they are not at the edge of the analysed area and partially protrude from the analysis area. The method according to the invention suggests a procedure in which it is not necessary either for an operator to intervene or to use derived parameters such as for example morphometric or densitometric parameters. surprisingly it turned out that it is even possible to examine image segments containing cells or cell complexes in close proximity with neural networks even when focussing on individual cells has not been carried out. This was unexpected since the known methods in the state of the art are based on the localisation, focussing and identification of individual objects such as cells, cell complexes or histological structures as individual objects.

Furthermore it has proven to be advantageous to classify the type of sample and, taking into account this classification, the neural networks examine whether cell types are present which do not belong to the type of sample or whether structural cell or tissue changes are present. In this procedure it has turned out to be important to digitalize the image of the sample and to divide the image points obtained into connected segments each of which can be examined individually.

The present invention is in the field of medical image diagnostics which includes tomography, ultrasound and microscopy. Among these methods microscopic diagnosis is the most important means for excluding or confirming malignant diseases. Therefore in gynaecological, urological or endoscopic examinations and operations samples are routinely sent to the pathological, cytological or haematological laboratory for oncological diagnosis. The sample material comprises cell smears, cell suspensions or components forming cells or structures which are obtained in biopsies or tissue sections.

In the current standard examination the doctor firstly decides at a cellular level whether all cell components are present, whether these are in a normal ratio to one another and whether the cell nucleus has a normal chromatin distribution. Furthermore it is analysed at this level whether unusual cell types are present. At the structural level the doctor examines whether the cell groups that are found correspond to the organ from which they were taken and whether cell types occur which are not typical for the examined tissue. In addition it is analysed whether the borders between the various tissue types are normal or disordered. The most frequent cause for such changes is the malignant transformation of cells.

Since the sought-after structural changes in the samples are not usually visible without staining, special stains are used. The preparations are stained by hand or using automated stainers during which it is also possible to use special immunological markers such as e.g. tumour marker antibodies. In the so-called in-situ hybridization special DNA probes which bind to the oncogene part of the cellular DNA are used to find tumour genes. The PCR method is a special embodiment of the detection of original tumour cells in which an adequate amount for various staining methods of a specific DNA or RNA is formed by an intermediate amplification step. The tissue components or cells labelled in this manner are then accessible to the microscopic analysis as described previously.

At the cellular level it is attempted to formulate decision rules with the aid of multivariate statistical methods so that the examination previously carried out by the doctor can be automated. An automation in this area is very important since the number of examinations continuously increases and there is often a lack of the necessary qualified laboratory staff. The early recognition of cancerous changes would contribute fundamentally to an improved patient prognosis. The automatic assessment of cellular and structural changes of cells and organs opens new possibilities in the early recognition of tumours and hence considerably increases the chances of healing.

The present invention is directed at these problems and proposes an automated method for examining tissue samples or body fluid samples.

Samples which can be examined with the method according to the invention are for example tissue sections, smears, cell smears and body fluids such as blood, urine, punctate fluid and such-like. For the examination the sample is mounted on a slide so that a thin layer of the sample is obtained that can be examined.

Within the scope of the invention cells, cell complexes, histological structures etc. are examined by neural networks. These entities are referred to collectively as cell objects in the following. These are also understood to include objects that are at the edge of the recorded image and only partially included.

The sample is analysed with an automatic microscope. Microscopes known in the state of the art (for example Wo 91/20048) have devices for adjusting the focussing as well as for adjusting desired image sections. The most current example of such a device for laterally moving the sample comprises a cross-table by which the slide can be shifted within a plane. In addition a microscope for carrying out the method according to the invention can also have devices for automatically changing lenses and filters.

The sensor of a video system is arranged in the image plane of the microscope. Current video cameras have a CCD array of ½ inch with 440,000 pixels. The frame-grabbers used for image recording yield arrays of 1024×1024 or 512×512 pixels. CCD arrays are known which provide grey values as the output value as well as those which yield colour values (red-green-blue values).

A system according to the invention for the automatic examination of samples additionally has an evaluation computer which is connected to the video system and also to the microscope. Evaluation computers for such an application have a so-called "frame-grabber" which serves to read the signal provided by the video system into the evaluation computer.

The evaluation computer in addition has devices for controlling the microscope in order to control focussing as well as a lateral shifting of the sample relative to the lens of the microscope.

The evaluation computer must have a high computing capacity in order to solve the present problem. In particular several neural networks are implemented in the evaluation computer.

Figure 1:
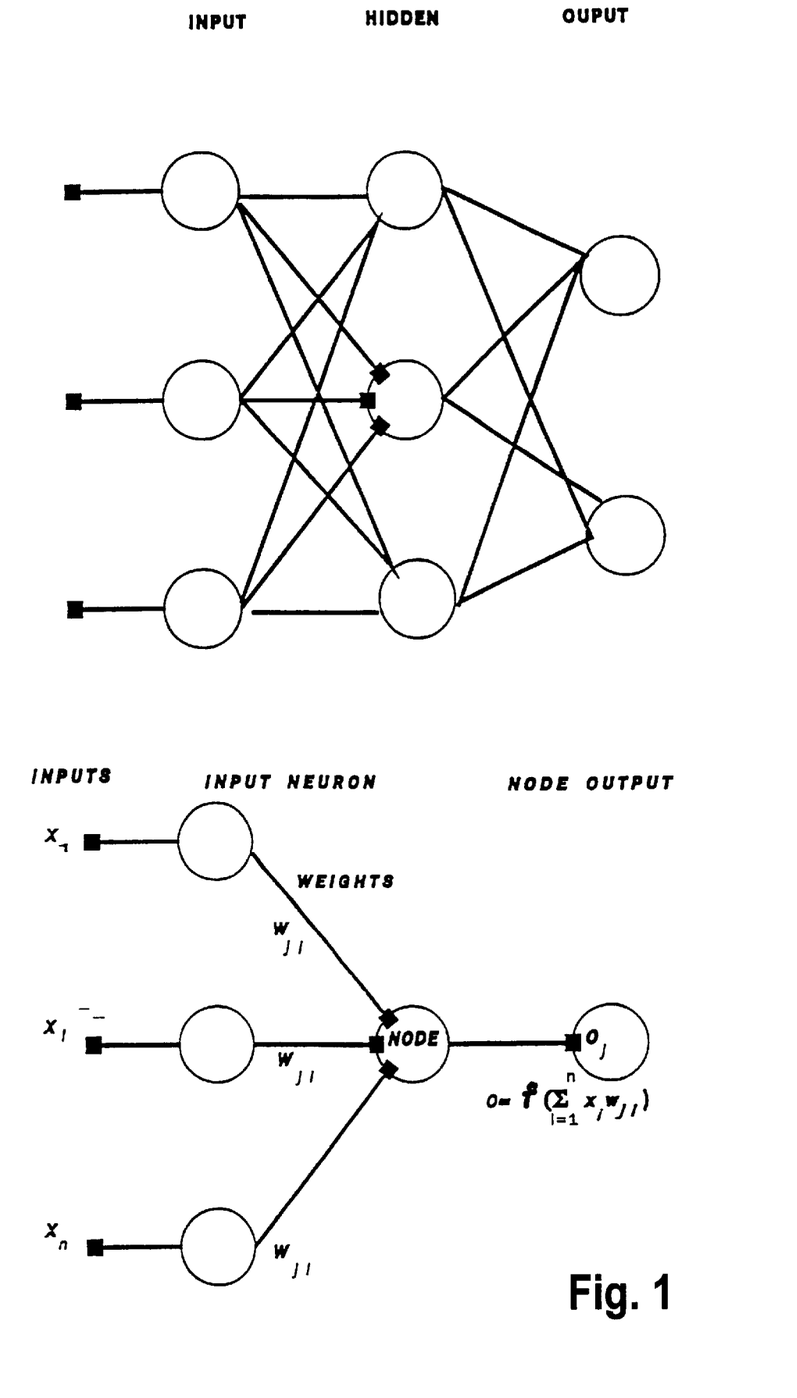
FIG. 1 shows the principal manner in which a neural network functions.

Neural networks are used as mathematical models of biological brain functions. It is attempted to simulate complex thinking and decision processes with the aid of computers by selecting suitable net topologies and processing functions. The principle findings on artificial neural networks are presented by Rummelhart and McCulloch in the book "Parallel distributed processing: Explorations in the microstructure of cognition". Today there are over 100 different network models as well as numerous connecting characteristics and functions. The principle manner in which a neural network functions is shown in FIG. 1. So-called input neurones are located on the input side of the neural network which are connected to hidden neurones. Each neurone has one or several weighted inputs either in the form of external signals or as an output from other neurones. Positive as well as negative weightings are possible. The sum of the weighted inputs is transferred via a transfer function into the output value or values which in turn control other neurones or serve as output values. The hidden neurones shown in FIG. 1 are connected with the output neurones. Of course the area of the hidden neurones can also have a considerably more complex structure and be composed of several interlinked levels. The totality of all neurones of a certain functionality is called a layer e.g. input layer. Of the organisation structures of neural networks known in the state of the art only the types Perceptron, Hopfield, Kohnen and Grossberg model are mentioned here. The most important parameters of a network, apart from the topology, are the neurone base potentials as well as the strength of the connections between the neurones. In order to set the parameters a representative training set is evaluated several times by the network. After each evaluation cycle the weightings and the base potentials are changed and newly set. This iteration is carried out until the average failure rate falls below a predetermined minimum or a previously defined problem related termination criterium is reached. The test set is also evaluated iteratively for control purposes.

The present invention is in particular characterized in that several neural networks with different tasks are used. For analysis by the neural networks the digitalized image is divided into connected segments preferably of the same size and the segments obtained are evaluated separately by the networks.

It is important that the examined sample is firstly classified according to type. This can either be carried out by an operator or the digitalized image of the sample is examined by a neural network ($NN_\alpha$).

In the method according to the invention an image of the sample is firstly recorded and individual image points are allocated to the digitalized signals of the image. The image points obtained are allocated to connected segments which are evaluated separately. The segments are examined by neural networks $NN_{\beta i}$ by feeding the input neurones with digitalized picture signals of the segment.

In a first type of neural networks $NN_{\beta 1}$ the neural network examines whether a cell, a cell complex, a tissue part or artefact structures are present in the respective segment. Alternatively or additionally it is possible to carry out a further analysis by a neural network $NN_{\beta 2}$ which examines whether the tissue of the sample is epithelium, endothelium, connective tissue or musculature or whether a body fluid is present. Furthermore analysis by a third neural network $NN_{\beta 3}$ is possible which examines whether a cell or a cell complex is present in the segment. Finally an additional examination by a fourth neural network $NN_{\beta 4}$ can be carried out which detects a cell object that juts out from the edge of the respective segment. If this is the case the entire cell object is analysed. If the cell object extends into other segments for which an image has already been recorded, the cell object can be examined by forming new segments in such a way that the cell object lies completely within one of these segments. However, if the cell object juts out of the image recorded by the video system, then it is necessary to record a further image which completely includes the cell object.

In an examination it is possible to use only one of the aforementioned analyses or to combine the networks with one another in a suitable manner. However, it is advantageous to use all four said neural networks for a sample.

In a method according to the invention the segments are additionally analysed with one or several neural networks $NN_{\gamma i}$ and classified as pathological if cell types are present which do not belong to the type of sample or if structural cell or tissue changes are present. In order to detect whether foreign cell types or structural changes are present it is important that the type of sample is incorporated in the analysis. In particular it is advantageous to select the neural networks $NN_{\gamma i}$ on the basis of the knowledge of the type of sample. Hence it is for example conceivable to provide sets of neural networks for each type of sample occurring in practice that have been trained for the special type of sample. Whether one or several networks are used to analyse the segments with the neural networks $NN_{\gamma i}$ depends on the complexity of the respective problem.

The respective sample was classified as pathological then a further examination is preferably carried out in which an image of the respective segment or segments in which peculiarities were found is recorded at a greater magnification and examined. The new recording is again divided into segments as already described and neural networks $NN_{\beta i}$ are used as already carried out for the lower resolution. Finally the neural networks $NN_{\gamma i}$ are also used for the recording at a greater magnification and again it is examined whether cell types are present which do not belong to the type of sample or whether structural cell/tissue changes are present. If this is the case then the diagnosis made for the image taken at a lower magnification is verified. It can also be arranged that the image with the higher magnification is shown directly on a monitor so that an experienced operator can carry out a visual analysis.

In addition to the methods already described, a subject matter of this patent application is a further method for automated microscopic examination which describes how an analysis by 3 different types of neural networks can be carried out in an efficient manner. The method already described and the following method can also be combined with one another.

Figure 5:
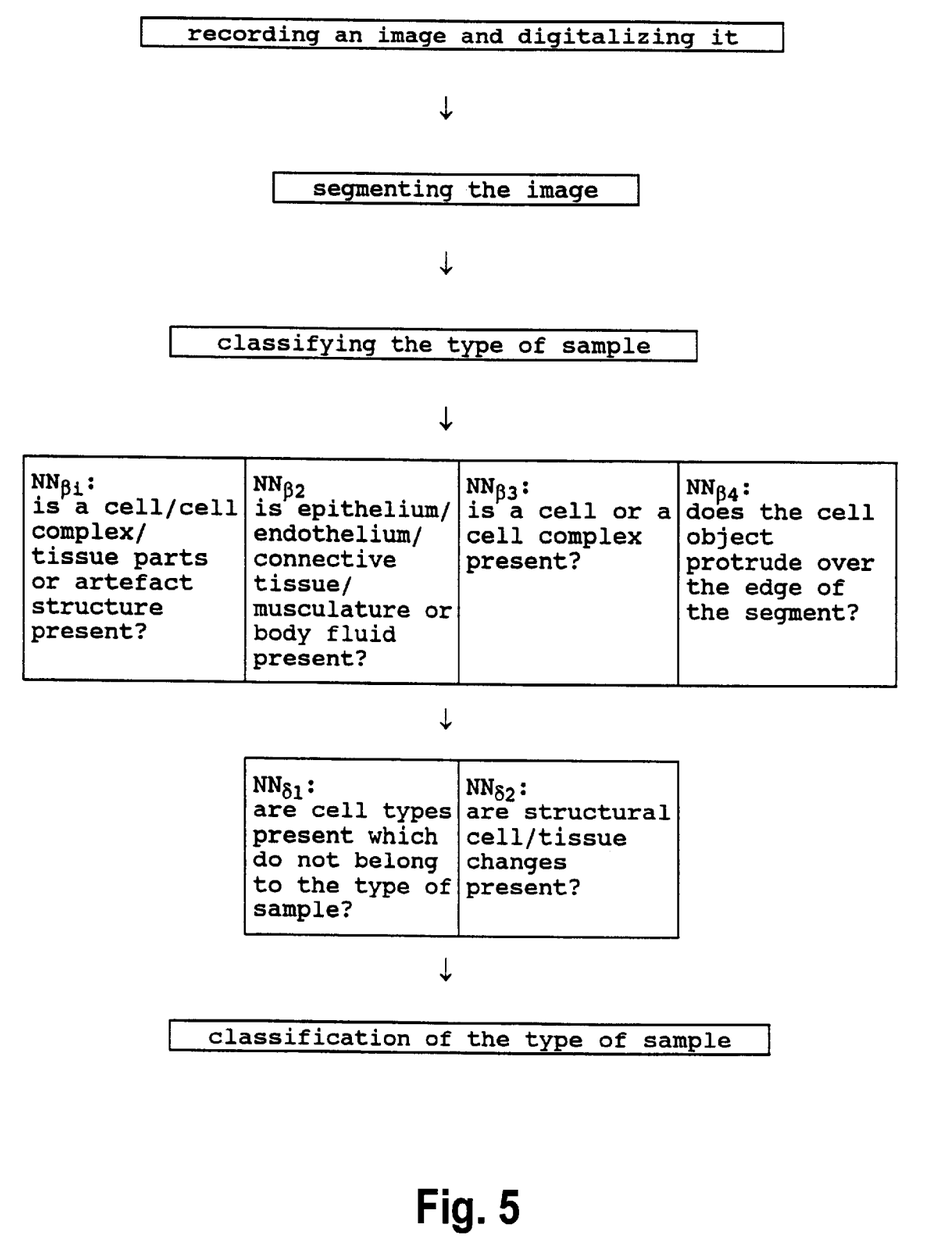
FIG. 5 is a flow diagram of the present invention.

The described method is shown in a more overall view in the flow diagram in FIG. 5.

In the second method according to the invention a first neural network serves to analyse the digitalized signals of the video system with regard to whether a cell object is located in the segment which was allocated to the input layer of the neural network. This first neural network ($NN_A$) preferably has a structure in which each output neurone is allocated to a 16×16 pixel image in the input field. This therefore results in a 32×32 output field for a CCD camera with 512×512 pixels. In the $NN_A$ and also in the neural networks $NN_B$ and $NN_C$ a digitalized image point is in each case assigned to an input neurone. Preferably a neural network according to the invention in each case has a single output neurone per segment.

Of course it is also possible to use NN with several output neurones per segment if the desired information can be read in a simple manner from these output neurones. The task of this first network is to determine in which of the segments a cell object is located. For this analysis it is necessary to appropriately train the neural network used. In particular it has proven to be advantageous to train the neural network with samples of the same type as those which are to be later analysed by the network. The training of neural networks to achieve the desired behaviour is well-known in the state of the art and is therefore not elucidated in more detail here.

As a result of the analysis, information is obtained in which segments cell objects are present. This is indicated by the activity of the output neurone or neurones which are assigned to each segment.

The segments in which a cell object has been detected are analysed by a second neural network ($NN_B$) by leading the digitalized signals of the respective segment to the input neurones of $NN_B$ and preferably allocating one output neurone to each of the segments whose activity indicates whether an individual cell or cell complex is present in the respective segment. Suitable neural networks can also be obtained for this application by training with samples of known composition. Analogously to the neural network A it is also advantageous in this case to carry out the training with samples of the same type. A procedure in which a segment is only analysed with the neural network B if previously a cell object has been detected with the neural network A in this segment, has the advantage that the number of segments which have to be evaluated can be greatly reduced which leads to a saving of computing time.

This procedure is then of particular advantage when only very few cell objects are present in the image (rare event detection).

Furthermore for the reliability of the method according to the invention it has proven to be necessary to check whether cell objects are at the image borders or are even only partially included in the image. In order to exclude this a third neural network ($NN_C$) is used which analyses the segments that lie at the image borders and in which a cell object was found. The neural network C yields information on whether a cell object is present at the image border in a particular segment. If this is the case then a further image of the sample is recorded in which the cell objects are completely included. For this the automatic microscope is steered by the evaluation computer in such a way that the sample and lens are laterally moved in opposite directions. This can for example be accomplished by a motor-driven crosstable. If the analytical steps have been carried out with the neural networks $NN_A$, $NN_B$ and $NN_C$ then the segments in which cell objects have been detected are recorded again at a higher magnification. The images obtained in this manner can for example be visually analysed by an operator. However, these recordings are advantageously evaluated by a further neural network ($NN_D$). This network analyses whether the sample can be rated as pathological.

The tree-like connections of the neural networks and the classifications and assessments occurring at the intersections result in ideal classification criteria that can be used to categorize normal and pathological samples. Hence a knowhow data base grows during the utilization of the system. Various such data bases which arise locally (i.e. in individual systems) can be brought together and yield a reference data base. The evaluating specialist can be offered normal or pathological samples from this reference data base as a reference for his own examinations.

The following advantageous embodiments relate to both said methods of examination.

A characteristic of the methods according to the invention is that the microscope is not focussed on individual cells or structures in any of the steps. It is only necessary to record images of suitable layers of the sample. The methods known in the state of the art for automated image analysis for cellular diagnostics localize cells or cell conglomerates and analyse these with regard to morphometric and densitometric parameters. It was therefore surprising that the methods according to the invention enable the detection of pathological structural changes with a high degree of certainty even without such focussing on individual objects.

It has proven to be particularly advantageous to record images from several layers of the sample in which the video system is not focussed on cells or cell groups. The information from overlying segments of the various layers can be combined to achieve a more accurate analysis.

A classification of the type of sample has already been described as advantageous since suitable neural networks can be selected on the basis of this information. Therefore the evaluation computer preferably has numerous different neural networks at its disposal which are adapted to various sample types. When the sample type is known, suitable neural networks can be automatically used for the evaluation steps of the method according to the invention. The classification of the sample itself can either be carried out by the user who classifies according to the origin or a further neural network can be used which is specialised for differentiating various sample types from one another.

For routine use it is preferable to label the slide on which the sample is located with regard to the type of sample (for example with a bar code). The information can be automatically read in (for example with a bar code reader) before the start of the examination procedure and this information can be transferred to the evaluation computer so that suitable neural networks are selected.

The magnifications at which the microscope operates is in the range of 30 to 200 and preferably at about 100 for the steps with the neural networks $NN_A$, $NN_B$ and $NN_C$. The recording at a higher magnification to analyse segments in which cell objects have been detected is carried out at a magnification of 200 to 600 preferably about 400.

It has proven to be advantageous in practice to use neural networks $NN_A$ and $NN_{\beta i}$ in which each output neurone is assigned a 16×16 input field.

The methods described above can also be modified in such a way that a three-dimensional, microscopic examination of tissue samples can be carried out with it. For this sections are prepared from a tissue sample which are each examined with the described methods. For this purpose the sections are prepared in a defined manner so that after the analysis is completed the evaluation results can be allocated to the original sites in the sample. Tissue sections are preferably used whose sectional planes are essentially parallel to one another. Such an examination of tissue samples was not possible with the previously available manual or partially automated methods in the state of the art. In a particularly favourable embodiment of this three-dimensional examination, the sections are labelled with two or several different preparation methods. For example a first section can be labelled with haematoxilin, a subsequent section with an immuno-histochemical label and a next section with an in-situ hybridization. The next section can then again be labelled with haematoxilin and so on.

If the data from several sections and preparations are logically integrated, then an analysis of these three-dimensional preparations is possible corresponding to a 4D slide-map. The same effect is also obtained when the sections of a biopsy sample are prepared alternately with several labelling processes in which for example antibodies with different epitope specificities and fluorescent labels are used. By the selection of individual RGB image components it is possible to obtain several three-dimensional microscopic images of the sample. Each fluorescent wavelength in this case corresponds to another sample characteristic. A 4D slide-map is formed by logical integration of the data which the doctor can leaf through with regard to sample topology as well as with regard to cell characteristics (type of label). It is possible to select various views of a sample by fading in or masking individual image data sets. This considerably aids the user of the system in verifying or falsifying diagnosis hypotheses.

A further application of the slide-maps is to generate various views from them with suitable software modules. This enables the observer to view the sample from various spatial directions. This is particularly important because various cell types especially in pathological samples tend to occur locally accumulated rather than homogeneously distributed and are thus easier to locate with the described procedure.

The use of the method according to the invention is further elucidated by the following application examples.

Haematological Cell Typing

In haematological cell typing the main tasks are as follows:

Determination of a quantitative or a qualitative blood count as well as detection and differentiation of malignant haematological diseases such as e.g. leukemia and lymphomas.

In order to carry out this analysis a blood smear or a sternum punctate smear is prepared by the prescribed methods and evaluated by the method according to the invention. In this application it is not absolutely necessary that the selected segments have to contain a whole cell and indeed they can also be evaluated when the segments contain only parts of the cell. Since the colour represents an important source of information in this application, the colour information of the pixels is preferably analysed by the RGB (red-green-blue) or by the HSI (hue-saturation-intensity) system.

Examination of Urine Sediments

In the examination of urine sediments a more qualitative diagnosis is required. In the case of the large cells (cylinders) of the urine sediment a reliable detection of these cells is of highest priority whereas for erythrocytes their number is more important.

Histological Examinations

Histological samples are nowadays analysed in very different ways depending on the clinical problem. Tissue samples from the operating room are for example analysed by rapid methods if the result is important for the progress of the operative procedure. A second type of samples is biopsies. In this case a sample is taken with a biopsy needle or excised with scissors if a solid mass is detected in the body during endoscopic ultrasound or X-ray tomography examinations. The analysis of such a sample generally takes about 1 week. The third type of samples are taken in an operation but not immediately analysed. The fourth type of samples are difficult to differentially diagnose and are sent to diagnostic centres. In this case DNA stains as well as immunohistochemical stains also come into consideration in addition to the direct analysis of histological or biopsy samples. Since the samples are very different it is particularly important for this application that a suitable neural network is selected for the respective type of sample. The network that carries out the final analysis differentiates between structures which are normally present in this type of tissue and those structures which are due to an abnormal change or are attributable to structures which are not normally present in this type of sample. Since the types of cases that can occur are very different, an analytical process is preferred in which the neural network localizes structures that have been recognized as unusual and these are displayed to the operator on a display so that a separate analysis can be carried out. On the other hand it is also possible to use differential diagnostic neural networks for this which are adapted to the possible case forms.

Immunohistochemical Examinations

The immunohistochemical reactions facilitate the differential diagnosis and contribute to the prognosis. At present there are a variety of immunohistochemical evaluation methods. In the case of cell suspensions one can use flow cytometry although reliable tumour markers or marker patterns are not yet available for this.

With the aid of TV image cytometry it is also possible to determine the immunohistochemical reactions of the individual cells not only qualitatively but also quantitatively. Up to now histological samples have been subsequently evaluated manually with a microscope where the time needed for stained preparations and preparations labelled with various antibodies is 5 to 30 minutes. The strength of the immunohistochemical reaction is marked "+" or "++" or "+++". For certain tumours a distinction is made between a positive nuclear and cytoplasmic reaction.

A system based on neural networks divides the image of the preparation stained with special antibodies into image segments and checks these segments for positive reactions. The neural network is preferably trained by the manufacturer and for each test a special training must be carried out. Depending on the difficulty of the problem to be solved it is also possible to use several, differently structured neural networks e.g. for different test procedures. If the analytical system receives the current requested test via a bar code or manual programming, the appropriate network type and the valid network parameters are selected automatically. The analysis can proceed very rapidly since the network only has to make a yes/no decision for an image segment.

An immunohistochemical evaluation can be carried out with neural networks after the sample has been stained with special antibodies. The image of the sample is divided into various image segments and these are checked for a positive reaction with the antibodies. In this application it is important to train a special neural network for each test. Depending on the difficulty of the problem to be solved it is also possible to use several differently structured neural networks for different test procedures. Especially in this application it is advantageous to communicate the current test to the analytical system via a bar code or via manual programming so that a suitable neural network can be used for the analysis.

In-situ Hybridization

In-situ hybridization serves to detect special DNA segments. In this method the cellular DNA is firstly unfolded, subsequently DNA probes provided with a labelling system are added. After the reaction is completed it is determined whether and how many probes a cell has taken up.

The most important tasks are to provide the labels and to analyse the reaction. Interest is increasing in automating the analysis of the reaction since meanwhile instruments have been developed for automatic sample preparation. With the aid of neural networks it is possible to simplify and carry out in a shorter period the second, work-intensive steps i.e. the image analysis. Moreover the analysis cannot only be carried out qualitatively (positive/negative) but also semiquantitatively in several steps.

Example 1

Analysis with a Neural Network A

Figure 2:
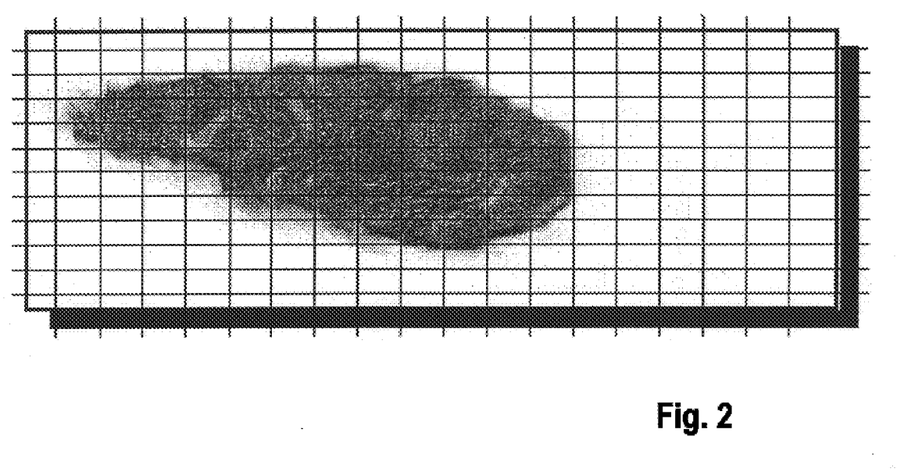
FIG. 2 shows an image of an object to be analysed which is located on a slide.
Figure 3:
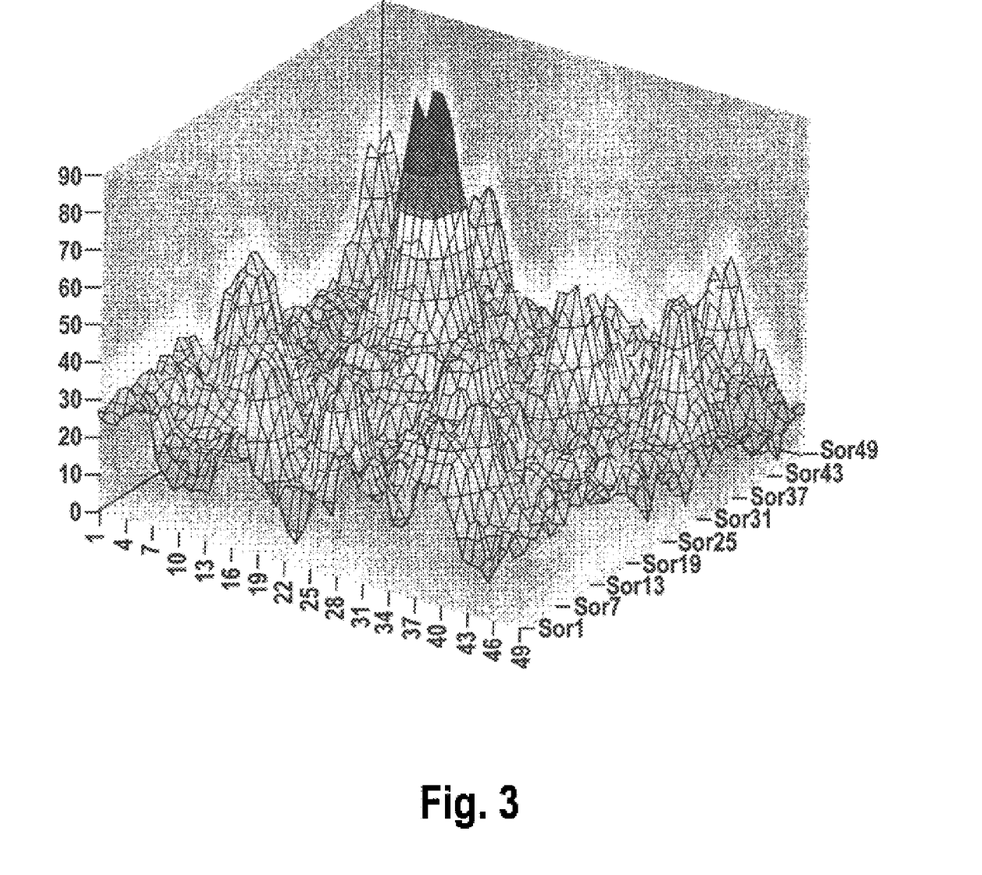
FIG. 3 shows an analysis of intensity distribution as described in Example 1.

FIG. 2 shows an image of an object to be analysed which is located on a slide. The image is read into an electronic memory for further processing. Image 3 shows the optical intensity distribution for the object located in the XY plane for the sample object on the Z axis. Instead of the monochromatic intensity measurement shown here, it is advantageous to measure the intensities of the colours red, yellow and blue and use these as a basis for a subsequent analysis.

Figure 4:
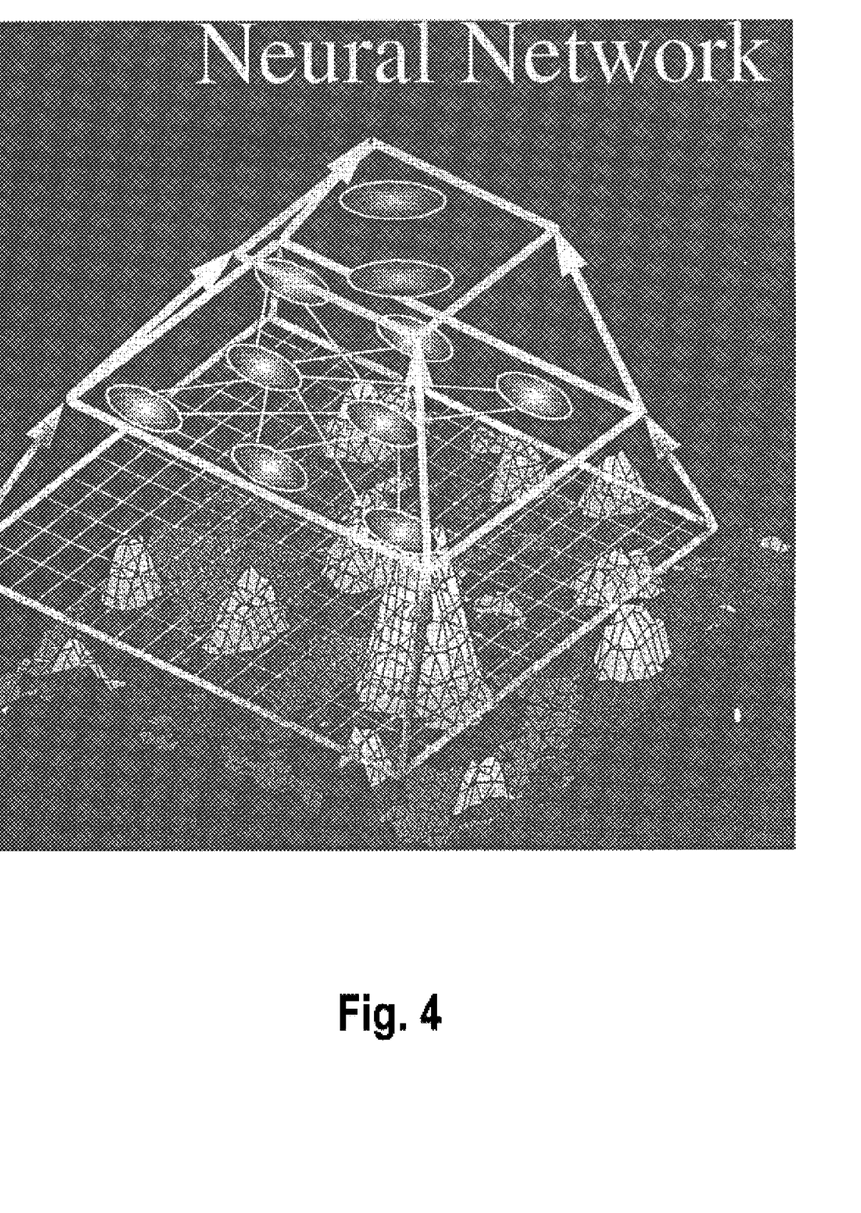
FIG. 4 is a schematic representation of intensity distribution as described in Example 1.

The analysis of the intensity distribution in FIG. 3 is shown schematically in FIG. 4. The raster drawn over the intensity distribution represents the partition of the image into segments. A neural network analyses the individual segments and checks whether a tissue sample is present in the respective segment. In further examinations only these image segments are taken into account.

For the example of a parenchymal tissue the intensity information is additionally examined for abnormalities using a neural network. Image segments in which such abnormalities were found, are classified with the aid of a further neural network which can differentiate between vascular objects, neurone complexes and direct pathological changes.

In the case of an epithelial/endothelial organ a neural network analyses whether the object to be analysed contains connective tissue, musculature, epithelium or endothelium. A further neural network analyses the borders of epithelium and connective tissue in order to detect invasive processes. Yet a further neural network can be used to examine whether the connective tissue contains epithelial/endothelial cell islets. A further neural network can search the segments for vascular or neurone complexes.

Example 2

Differentiation of Tissue Types with the Aid of Neural Networks

Preparing a Microscopic Image of the Sample

In this example a sample from a stomach biopsy is examined, the sample size is 3 mm×8 mm and haematoxilineosin is used for staining. A Zeiss Axioplan 2 MOT microscope is used to automatically take the picture and an Olympus BH2 microscope is used to manually record the picture. A Grundig ½" CCD camera is used for colour pictures and it can also yield black/white images. Alternatively a camera from the "Stemmer Datentechnik" can be used. Without compression the data volume is ca. 1 Mbyte for an image section of 40 μm×40 μm, with the aid of JPEG compression the memory requirement can be reduced to about 10–20% without significant losses of image information. The individual images are stored in such a way that it is possible to electronically search for image contents over all segments.

Simulation of a Decision Tree with Neural Networks

A neural network A checks all partial images for the presence of biological material, all "empty" segments are discarded/erased. The result of this analysis is a segmented "map" of the slide in which the position of the tissue sample is plotted. This slide map is stored in the computer and serves as a reference for further examinations and classifications.

A neural network B is used to examine whether the segments contain an epithelium. If the assessment is positive the decision tree branches into the neural networks B1 and B2. Network B1 checks whether other tissue types are also present and whether a border region of the epithelium is present. Network B2 differentiates between upper and lower epithelial regions.

If epithelium is not present the neural network C checks whether the segment contains connective tissue or musculature.

The further examination of the image segments is carried out by the neural networks D and E. Network D searches for epithelium with pathological cells or cell groups. Network E checks the connective tissue segments for possible inclusions of epithelial islets.

Summary of the Individual Analyses

The results of the individual analyses are entered stepwise in the slide map and are available to the doctor as a decision basis. For the visualization, the various tissue types are represented by different colours e.g. green for epithelium, yellow for connective tissue, orange for musculature, pathological areas are marked red. The advantage of this representation is that in addition to differentiating between the various tissue types it is also possible to see their relative size and position with respect to one another. With the aid of an appropriate analytical tool it is in addition possible to call up an image segment directly by a mouse click on the slide map.

Example 3

Detection of Proliferating Cells with the Aid of Neural Networks

Microscopic Image of the Sample

In this example a haematoxilin-stained preparation from a stomach biopsy is examined with the PCNA antibody system (the antibodies are directed against the proliferation cellular nuclear antigen and are labelled with the avidin-biotin-peroxidase system). Cell nuclei with a positive reaction stain light-brown and non-reactive cell nuclei adopt a light-blue colouration.

The automatic recording of the image segments is carried out as described in example 2. A Grundig camera 830I is used which provides a black/white image as well as the three RGB colour components.

Simulation of the Decision Tree with Neural Networks

On the basis of the black/white images a neural network A checks which segments are derived from the epithelium. These are then examined by the neural network B for centres with positive staining.

Summary of the Individual Analyses

The results of the analyses are entered in the slide map in which for example the positive epithelium regions are represented brown, the negative are green and the regions without epithelium are yellow. Metastases can be rapidly and reliably detected in the slide map.

Example 4

Spatial distribution of Tissue Types in a Preparation

Several parallel sections at defined distances are taken from a biopsy sample. Sample preparation, image recording and analysis by the various neural networks are carried out as described in example 3. The analysis is carried out such that the data of the individual sections are logically integrated and a three-dimensional representation of the biopsy sample collected is obtained with the aid of an extended analysis program (3-D slide map).

What is claimed is:

1. A method for automated microscopic examination of samples on a slide, said method comprising the steps of:
providing an automatic microscope, a video system, and an evaluation computer with a first and a second neural network, wherein each of said first and second networks each have input neurones;
recording, in a first recording step, a first image of a sample with the video system, and allocating digitized signals to individual image points of the first image;
evaluating the first image and individual image points to classify the sample by type;
dividing, in a first dividing step, the individual image points into connected segments;
analyzing, in a first analyzing step, each segment with said first neural network, wherein image signals of each segment are input to the input neurones of the first neural network;
analyzing the connected segments with the second neural network; and
classifying the sample as pathological if cell types are present which do not belong to the type of sample, and/or if structural cell/tissue changes are present in the sample.

2. A method as recited in claim 1, wherein said classifying step is performed by the second neural network.

3. A method as recited in claim 1, wherein said classifying step is performed by a third neural network.

4. A method as recited in claim 1, wherein the first neural network performs a step of examining whether at least one of a cell, a cell complex, tissue parts, and artifact structures are present in said each segment.

5. A method as recited in claim 1, wherein a third neural network examines whether the sample is one of epithelium, endothelium, connective tissue, musculature, or a body fluid.

6. A method as recited in claim 1, wherein a third neural network examines whether one of a cell and a cell complex is present in said each segment.

7. A method as recited in claim 1, wherein a third neural network analyzes each segment, and recognizes when a cell object protrudes over an edge of said each segment, and wherein the cell object is examined when the protrusion is recognized.

8. A method as recited in claim 1, wherein when the sample is classified as pathological, a second recording step is performed wherein a second image of the sample is recorded at an increased magnification, and wherein a second dividing step and a second analyzing step are performed on the second image.

9. A method as recited in claim 8, wherein the first recording step is performed with a magnification of 30 to 200, and the second recording step is performed at a magnification of 200 to 600.

10. A method as recited in claim 8, wherein the first recording step is performed at a magnification of approximately 100, and wherein the second recording step is recorded at a magnification of approximately 400.

11. A method as recited in claim 1, wherein the video system records images of the sample in at least two layers.

12. A method as recited in claim 1, wherein the first and second neural networks are determined based upon the classified type of the sample.

13. A method as recited in claim 1, further comprising a step of providing, as the sample, a tissue section stained with one of immunohistochemical stains and in-situ hybridization before the recording step, and wherein the recording, evaluating, dividing, analyzing, and classifying steps are performed based upon the staining.

14. A method as recited in claim 13, comprising a step of amplifying at least one of DNA and RNA in the sample prior to the staining step.

15. A method as recited in claim 1, comprising the steps of repeating the recording, evaluating, dividing, analyzing and classifying steps for first and second samples, wherein output signals from the analyzing steps are integrated to form a three-dimensional image.

16. A method as recited in claim 15, wherein said first and second samples are labelled using first and second labelling methods, said first and second labelling methods being different.

17. A method for automated microscopic examination of samples on a slide, said method comprising the steps of:
provided an automatic microscope, a video system, and an evaluation computer with at least first, second, and third neural networks, wherein each of said first, second and third neural networks have input neurones and output neurones;
recording, in a first recording step, an image of a sample with the video system, and allocating digitized signals to individual image points of the sample;
dividing, in a first dividing step, the individual image points into connected segments;
analyzing, in a first analyzing step, each segment of said connected segments with the first neural network, wherein the individual image points of the segment are input to the input neurones of the first neural network, and wherein at least one output neurone of the first neural network is assigned to each connected segment having activity which indicates that a selected cell object is present in said each segment;
analyzing, in a second analyzing step, said each segment in which the cell object has been detected, wherein the individual image points of said each segment are led to the input neurones of the second neural network, and wherein at least one output neurone of said second neural network is assigned to each segment having activity which indicates that an individual cell or cell complex is present therein;
analyzing, in a third analyzing step and using the third neural network, segments located on image borders of the image, wherein the image points of each of the segments analyzed by the third neural network are led to the input neurones of the third neural network, and wherein the third neural network yields information on whether the cell object is located on the image borders;
recording, in a second recording step, second images containing complete cell objects for the segments identified by the third neural network if objects have been detected which are located on the image borders; and
recording, in a third recording step, the segments identified to have a cell object with higher magnification.

18. A method as recited in claim 17, wherein a second image created in said third recording step is analyzed by a fourth neural network, wherein the fourth neural network outputs information regarding whether the sample is pathological.

19. A method as recited in claim 18, further comprising a step of classifying the sample by type, and wherein the fourth neural network utilizes the type classification in determining whether the sample is pathological.

20. A method as recited in claim 19, wherein said classifying step is performed by an operator.

21. A method as recited in claim 19, wherein the classification step is performed by a fifth neural network.

22. A method as recited in claim 19, wherein the fourth neural network is determined based upon the type of sample determined in the classification step.

23. A method as recited in claim 19, wherein the first, second, third, and fourth neural networks are determined based upon the classified type of the sample.

24. A method as recited in claim 19, comprising a step of identifying segments which contain cells from a type which is different from the classified type of the sample.

25. A method as recited in claim 18, further comprising a step of determining whether cells, cell complexes, or intercellular structures are present in the sample which are not present in non-pathological samples of a same type, thereby recognizing the sample as pathological.

26. A method as recited in claim 18, comprising a step of identifying connected segments which contain unexpected cells therein.

27. A method as recited in claim 17, wherein the video system records images of the sample in at least two layers.

28. A method as recited in claim 17, further comprising a step of providing, as the sample, a tissue section stained with one of immunohistochemical stains and in-situ hybridization before the recording step, and wherein the recording, evaluating, dividing, and analyzing steps are performed based upon the staining.

29. A method as recited in claim 28, comprising a step of amplifying at least one of DNA and RNA in the sample prior to the staining step.

30. A method as recited in claim 17, wherein the first recording step is performed with a magnification of 30 to 200, and the second recording step is performed at a magnification of 200 to 600.

31. A method as recited in claim 17, wherein the first recording step is performed at a magnification of approximately 100, and wherein the second recording step is recorded at a magnification of approximately 400.

32. A method as recited in claim 17, wherein each output neurone of said first neural network comprises a 16×16 input field.

33. A method as recited in claim 17, wherein said step of providing the video system comprises providing a CCD camera including a 440,000 pixel CCD array.

34. A method as recited in claim 17, comprising the steps of repeating the recording, evaluating, dividing, analyzing and classifying steps for first and second samples, wherein output signals from the analyzing steps are integrated to form a three-dimensional image.

35. A method as recited in claim 34, wherein said first and second samples are labelled using first and second labelling methods, said first and second labelling methods being different.

36. A system for automated microscopic examination of samples on a slide, said system comprising:
recording means for recording a first image of a sample, said recording means allocating digitized signals to individual image points of the first image;
evaluating means for evaluating the first image and individual image points to classify the sample by type;
dividing means for dividing the individual image points into connected segments;
a first neural network connected to said dividing means, said first neural network including input neurones receiving image signals of each segment;
a second neural network connected to said dividing means for analyzing the connected segments; and
classifying means for classifying the sample as pathological if cell types are present which do not belong to the type of sample, and/or if the structural cell/tissue changes are present in the sample.

37. A system for automated microscopic examination of samples on a slide, said system comprising:
recording means for recording an image of a sample, said recording means allocating digitized signals to individual image points of the sample;
dividing means for dividing the individual image points into connected segments;
a first neural network connected to said dividing means, said first neural network including input neurones and output neurones, said input neurones receiving the individual image points of each segment of the connected segments, and wherein at least one output neurone is assigned to each connected segment having activity which indicates that a selected cell object is present in said each segment;

a second neural network having input neurones and output neurones and being connected to said dividing means, wherein the individual image points of said each segment are lead to the input neurones of the second neural network, and wherein at least one output neurone of the second neural network is assigned to each segment having activity which indicates that an individual cell or cell complex is present therein;

a third neural network having input neurones and output neurones and being connected to said dividing means, wherein the image points of each of the segments are provided to the input neurones of the third neural network, and wherein the third neural network yields information on whether the cell object is located on the image borders;

wherein the recording means is connected to the third neural network, and records second images containing complete cell objects for the segments identified by the third neural network if objects have been detected which are located on the image borders, and also records the segments identified to have a cell object with higher magnification.

* * * * *